(12) United States Patent
Awad et al.

(10) Patent No.: US 11,890,432 B2
(45) Date of Patent: Feb. 6, 2024

(54) SHAPED PULL WIRE FOR DEFLECTABLE VASCULAR CATHETER SHEATH

(71) Applicant: Oscor Inc., Palm Harbor, FL (US)

(72) Inventors: Ramy Awad, Palm Harbor, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 269 days.

(21) Appl. No.: 17/342,075

(22) Filed: Jun. 8, 2021

(65) Prior Publication Data

US 2021/0379334 A1 Dec. 9, 2021

Related U.S. Application Data

(60) Provisional application No. 63/036,100, filed on Jun. 8, 2020.

(51) Int. Cl.
*A61M 25/01* (2006.01)

(52) U.S. Cl.
CPC .... *A61M 25/0147* (2013.01); *A61M 25/0136* (2013.01)

(58) Field of Classification Search
CPC .......... A61M 25/0147; A61M 25/0136; A61M 2025/015
See application file for complete search history.

(56) References Cited

U.S. PATENT DOCUMENTS

| 5,254,088 | A | * | 10/1993 | Lundquist | A61M 25/0136 604/95.04 |
|---|---|---|---|---|---|
| 6,829,497 | B2 | * | 12/2004 | Mogul | A61M 25/0147 600/374 |
| 8,182,467 | B2 | * | 5/2012 | Nguyen | A61M 25/0043 604/95.04 |
| 9,498,602 | B2 | | 11/2016 | Osypka et al. | |
| 9,572,957 | B2 | | 2/2017 | Osypka et al. | |
| 9,907,570 | B2 | * | 3/2018 | Osypka | A61B 90/94 |
| 9,913,684 | B2 | | 3/2018 | Osypka | |
| 10,188,834 | B2 | * | 1/2019 | Zhang | A61M 25/0147 |
| 10,258,763 | B2 | * | 4/2019 | Grasse | B29C 48/022 |
| 10,814,099 | B2 | * | 10/2020 | Funk | A61B 17/00 |
| 11,357,451 | B2 | * | 6/2022 | Osypka | A61L 29/02 |
| 2006/0253070 | A1 | * | 11/2006 | Butler | A61M 25/0136 604/95.04 |
| 2007/0005008 | A1 | * | 1/2007 | Honebrink | A61M 25/0147 604/95.04 |
| 2007/0270679 | A1 | * | 11/2007 | Nguyen | A61M 25/0043 600/585 |

(Continued)

*Primary Examiner* — Katherine H Schwiker
*Assistant Examiner* — Adam J. Cermak
(74) *Attorney, Agent, or Firm* — Michael F. Scalise

(57) ABSTRACT

A deflectable vascular catheter includes a proximal handle assembly, an elongated sheath extending distally from the proximal handle assembly and including a deflectable distal end portion, an actuation mechanism operatively associated within an interior cavity of the proximal handle assembly for deflecting the distal end portion of the sheath, an anchor ring located at a distal end of the deflectable distal end portion of the sheath, and a pull wire extending from the actuation mechanism to the anchor ring. The pull wire has a non-circular cross-section and is laser welded to an exterior surface of the anchoring ring.

17 Claims, 3 Drawing Sheets

(56) References Cited

U.S. PATENT DOCUMENTS

| | | | |
|---|---|---|---|
| 2007/0299424 A1* | 12/2007 | Cumming | A61M 25/0012 |
| | | | 604/527 |
| 2011/0282176 A1* | 11/2011 | Tegg | A61B 5/283 |
| | | | 604/95.04 |
| 2012/0130218 A1* | 5/2012 | Kauphusman | A61B 5/6852 |
| | | | 600/585 |
| 2020/0206482 A1* | 7/2020 | Calhoun | A61M 25/0045 |
| 2022/0023595 A1* | 1/2022 | Bataille | A61M 25/0108 |
| 2022/0151464 A1* | 5/2022 | Bendory | A61B 1/0058 |
| 2022/0183868 A1* | 6/2022 | Ichimura | A61M 25/0054 |

\* cited by examiner

SHAPED PULL WIRE FOR DEFLECTABLE VASCULAR CATHETER SHEATH

CROSS-REFERENCE TO RELATED APPLICATION

The subject application claims the benefit of priority U.S. Provisional Application No. 63/036,100 which was filed on Jun. 8, 2020, the contents of which is incorporated by reference herein in its entirety.

BACKGROUND OF THE INVENTION

1. Field of the Invention

The subject invention is directed to surgical instrumentation, and more particularly, to a non-circular pull wire assembly for a deflectable vascular catheter sheath.

2. Description of Related Art

Steerable catheters or guiding sheaths are well known in the art. They are used for vascular access and the delivery of therapeutic devices such as stents, anchors and drugs to targeted areas in the vascular system of the human body. They can also be used as vascular ablation catheters, for example in renal ablation procedures.

Steerable or deflectable sheaths can be uni-directional or bi-directional, and they are typically available in sheath ID French sizes ranging from 4 F to 20 F. These devices can be designed with deflection angles that vary from 90 degrees to 270 degrees, and they can be designed with various tip formations, shaft stiffness and handle configurations.

Examples of steerable catheters or guiding sheaths with deflectable distal end portions that are configured for use in conjunction with the subject invention are disclosed in commonly assigned U.S. Pat. Nos. 9,498,602; 9,572,957; 9,907,570; and 9,913,684, the disclosures of which are herein incorporated by reference in their entities.

The deflection curve of the distal end of the catheter sheath allows a physician to access complex vasculature in a very short period of time, as compared to the use of a non-deflectable sheath that has a fixed distal curvature. Typically, deflectable sheaths feature a deflection curve whereby the distal tip deflects in a single plane. Others can deflect in multiple planes.

Most steerable catheters or guiding sheaths use pull wires to effectuate the defection of the distal end portion of the sheath. These pull wires have a round cross-section, can have a diameter of between 0.004" to 0.011" and they are typically secured to an anchor ring that is located at the distal end of the sheath (See FIG. 3). Under tension, the pull wire fastened to the anchor ring at a tangential point on its periphery contracts at the specified deflection area of the instrument. These anchor rings have a significantly increased width as compared to their wall thickness. The current accepted practice for fastening the round pull wire to the anchor ring is laser welding. This avoids large heat affected zones and distortion.

However, laser welding the two components together needs somewhat advanced knowledge, because it requires minimal gaps between the two substrates being welded. This is usually accomplished with creative positioning of the laser welding nozzle and elegant use of fixtures. Any gap can potentially cause the weld to fail, since laser welding does not add any material but is dependent on substrate flow.

Additionally, one of the key features for most catheter is reducing its wall thickness. Round pull wires tend to increase the wall thickness of the catheter due to the diameter of the wire. If a geometry exists to reduce the thickness of the pull wire while maintaining the cross-sectional area (thus preserving strength), then this would be a key benefit.

SUMMARY OF THE INVENTION

The subject invention is directed to a new and useful deflectable vascular catheter that overcomes the problems and difficulties associated with using round pull wires, as described above. More particularly, the catheter includes a proximal handle assembly, an elongated sheath extending distally from the proximal handle assembly and including a deflectable distal end portion, an actuation mechanism operatively associated within an interior cavity of the proximal handle assembly for deflecting the distal end portion of the sheath, at least one anchor ring located at a distal end of the deflectable distal end portion of the sheath, and at least one shaped pull wire extending from the actuation mechanism to the at least one anchor ring, wherein the at least one pull wire has a non-circular cross-section and is attached to an exterior peripheral surface of the at least one anchoring ring.

Preferably, the at least one shaped pull wire is laser welded to the exterior peripheral surface of the at least one anchor ring. In one embodiment of the invention, the at least one shaped pull wire has a semi-circular cross-section. In another embodiment of the invention, the at least one shaped pull wire has a semi-circular cross-section that is concave. It is envisioned that a plurality of shaped pull wires can be stacked upon one another, each having a non-circular cross-section. Here, each shaped pull wire can have a different non-circular cross-section, or each shaped pull wire can have a common non-circular cross-section. It is envisioned that each pull wire can be attached to a respective anchor ring. It is envisioned that the second one of the plurality of pull wires is attached at two non-adjacent points to the anchoring ring.

In an embodiment of the invention, the actuation mechanism includes a linear drive screw that is mounted for reciprocal axial movement within the interior cavity of the proximal handle assembly, and a rotatable control knob operatively associated with a distal end portion of the proximal handle assembly for moving the linear drive screw.

The subject invention is also directed to a uni-directional deflectable vascular catheter including a proximal handle assembly, an elongated sheath extending distally from the proximal handle assembly and including a deflectable distal end portion, an actuation mechanism operatively associated within an interior cavity of the proximal handle assembly for deflecting the distal end portion of the sheath in one direction, an anchor ring located at a distal end of the deflectable distal end portion of the sheath, and a shaped pull wire extending from the actuation mechanism to the anchor ring, wherein the shaped pull wire has a non-circular cross-section and is attached to an exterior peripheral surface of the anchor ring.

The subject invention is also directed to a bi-directional deflectable vascular catheter including a proximal handle assembly, an elongated sheath extending distally from the proximal handle assembly and including a deflectable distal end portion, an actuation mechanism operatively associated within an interior cavity of the proximal handle assembly for deflecting the distal end portion of the sheath in two directions, an anchor ring located at a distal end of the deflectable distal end portion of the sheath, a first shaped pull wire extending from the actuation mechanism to the anchor ring, wherein the first shaped pull wire has a non-circular cross-section and is laser welded to an exterior peripheral surface of the anchor ring, and a second shaped pull wire extending from the actuation mechanism to the anchor ring, wherein the second shaped pull wire has a non-circular cross-section and is laser welded to an exterior peripheral surface of the anchor ring, at a location opposite from the first shaped pull wire.

These and other features of deflectable vascular catheter and the shaped pull wires of the subject invention will become more readily apparent to those having ordinary skill in the art to which the subject invention appertains from the following description of the drawings.

BRIEF DESCRIPTION OF THE DRAWINGS

So that those skilled in the art will readily understand how to make and use the deflectable vascular catheter of the subject invention without undue experimentation, reference may be made to the figures wherein.

ENABLING DESCRIPTION OF THE CLAIMED INVENTION

Figure 1:
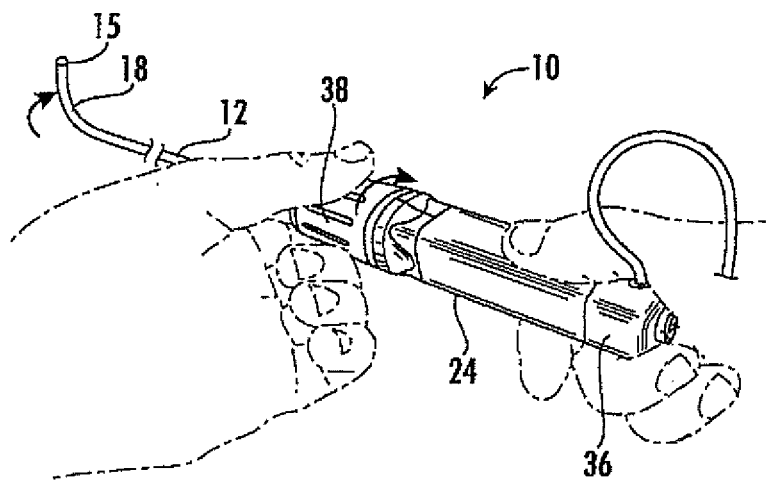
FIG. 1 is a perspective view of a vascular catheter having a sheath with a deflectable distal end portion deflected in a first direction.

Referring now to the drawings, there is illustrated in FIG. 1 a deflectable vascular catheter 10 of the type disclosed in commonly assigned U.S. Pat. No. 9,498,602, which is incorporated herein by reference. It includes a proximal handle assembly 24 and an elongated sheath 12 extending distally from the proximal handle assembly 24. The handle assembly 24 includes a main body portion 36 and a rotatable deflection control knob 38.

The sheath 12 has a deflectable distal end portion 18. An actuation mechanism controlled by a rotational control knob 38 is operatively associated within proximal handle assembly 24 for steering or otherwise deflecting the distal end portion 18 of the sheath 12. The actuation mechanism can include one or more linear drive screws or the like. An anchor ring (not shown in FIG. 1) is located at the distal end in the vicinity of the tip 15 of the deflectable distal end portion 18 of the sheath 12.

Figure 2:
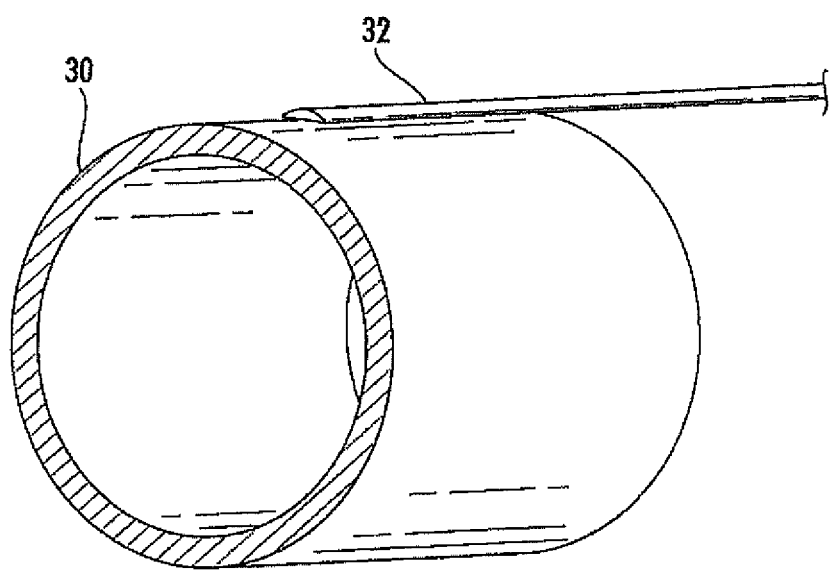
FIG. 2 is perspective view of anchor ring with a shaped pull wire having a semi-circular cross-section welded to an outer peripheral surface thereof.

The anchor ring is best seen in FIG. 2 and is designated by reference numeral 30. It has a significantly increased width as compared to its wall thickness. A non-circular shaped pull wire 32 extends from the actuation mechanism, through the wall of the sheath 12 to the distal anchor ring 30. The non-circular shaped pull wire 32 is laser welded to an exterior peripheral surface of the anchor ring 30. In a bi-directional catheter sheath, a second non-circular shaped pull wire would be laser welded to the anchor ring 30, at a location opposite from pull wire 32. The subject invention contemplates the use of shaped pull wires in uni-directional and bi-directional deflectable vascular sheaths.

Figure 4:
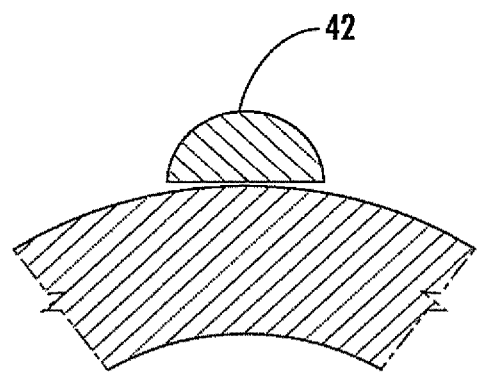
FIG. 4 is cross-sectional view of a section of an anchor ring with a shaped pull wire having a semi-circular cross-section welded thereto.

Referring now to FIG. 4, there is shown a shaped pull wire 42 constructed in accordance with the subject invention that is laser welded to an exterior peripheral surface of an anchor ring. Pull wire 42 has a semi-circular or D-shaped cross-sectional configuration. The dimensions of the shaped pull wire 42 can vary by design, including its outer radius of curvature, its radial thickness or height and its base width or diameter.

Figure 3:
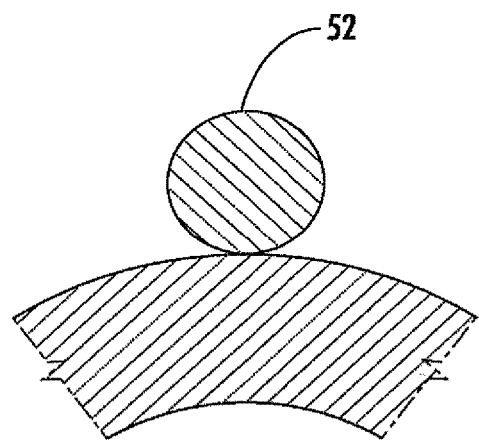
FIG. 3 is cross-sectional view of a section of an anchor ring with a conventional circular pull wire welded thereto.

As compared to the round pull wire 52 shown in FIG. 3, there is little if any gap between the semi-circular pull wire 42 and the anchor ring shown in FIG. 4, providing a minimal gap between the two substrates being welded together. This reduces the likelihood that the weld will fail. Furthermore, it can be really appreciated by comparing the pull wire assemblies shown in FIGS. 3 and 4 that the use of a semi-circular or D-shaped pull wire 42 will result in a reduced wall thickness for a catheter sheath, as compared to the conventional round pull wire 52 shown in FIG. 3. That is, round pull wires tend to increase the wall thickness of the catheter due to the diameter of the wire, which can range from 0.004 to 0.011 inches.

Figure 5:
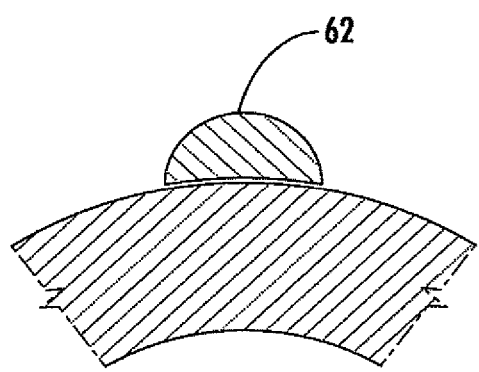
FIG. 5 is cross-sectional view of a section of an anchor ring with a shaped pull wire having a semi-circular cross-section that is slightly concave welded thereto.
Figure 6:
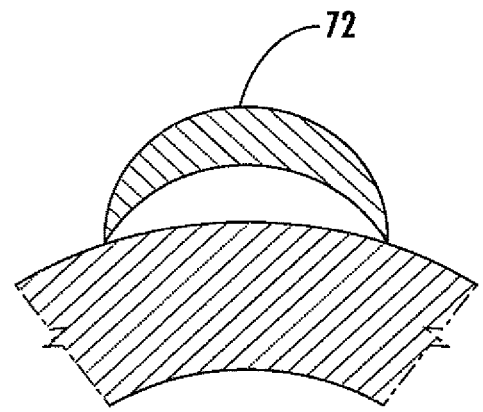
FIG. 6 is cross-sectional view of a section of an anchor ring with a shaped pull wire having a semi-circular cross-section that is deeply concave welded thereto.

Referring now to FIG. 5, there is illustrated a shaped pull wire 62 that has a semi-circular cross-section that is slightly concave or arch shaped, whereas FIG. 6 shows a shaped pull wire 72 that has a semi-circular cross-section that is more deeply concave than the one shown in FIG. 5 attached at two non-adjacent points to the anchoring ring. These shaped pull wires also minimize the gap that exists between the two substrates being welded, as compared to the conventional round pull wire shown in FIG. 3.

Figure 7:
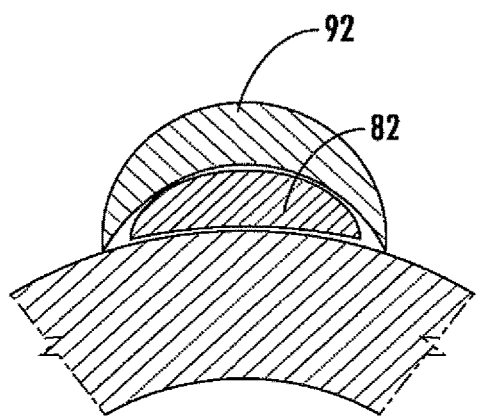
FIG. 7 is cross-sectional view of a section of an anchor ring with two shaped pull wires stacked together and welded thereto, with each shaped pull wire having a different non-circular cross-section.

It is envisioned that a plurality of shaped pull wires 82 and 92 can be stacked upon one another, each having a non-circular cross-section, as shown in FIG. 7. As depicted here, the two stacked pull wire have different non-circular cross-sectional shapes, with the inner semi-circular pull wire 82 having a shallow concavity and the outer semi-circular pull wire 92 having a much deeper concavity than the inner pull wire 82.

Figure 8:
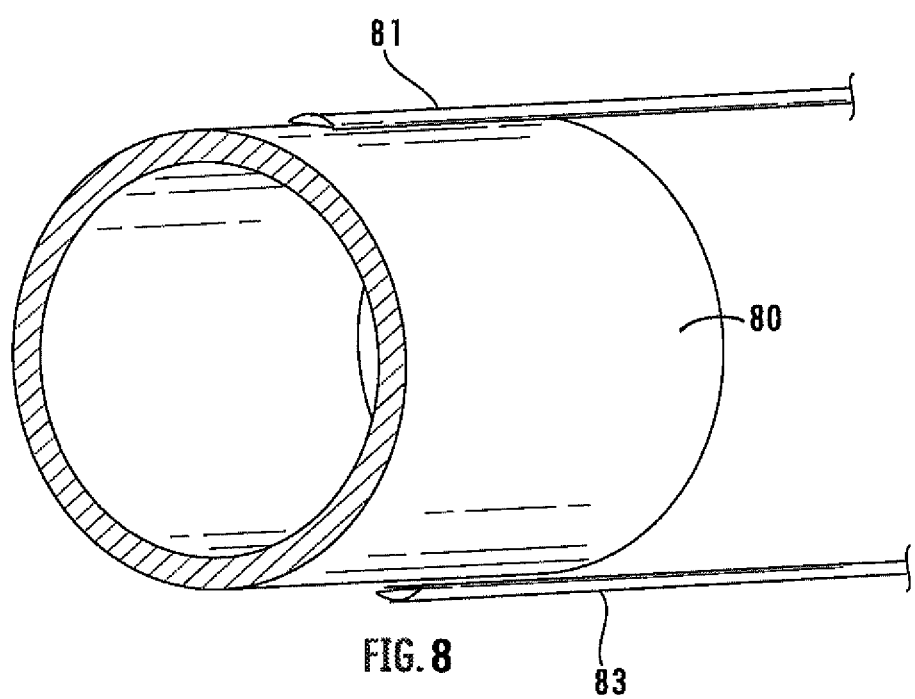
FIG. 8 is perspective view of anchor ring of a bi-directional catheter sheath, showing a second non-circular shaped pull wire would be attached to the anchor ring, at a location opposite from first pull wire.

Referring now to FIG. 8, a bi-directional catheter sheath is showing having, a second pull wire attached at location 83 to the anchor ring 80, at a location opposite from pull wire 81. Each of the pull wires shown in FIG. 8 are meant to be representative and can include any of the configurations mentioned previously and shown in FIGS. 4-7.

Alternatively, each stacked pull wire can have a common non-circular cross-section, and each shaped pull wire can be attached to a respective anchor ring to provide different pull wire effects. Thus multiple different or similar shaped pull wires and/or multiple anchor rings can provide different pull wire effects with respect to the deflectable distal end portion of the vascular catheter.

While the deflectable vascular catheter of the subject disclosure has been shown and described with reference to preferred embodiments, those skilled in the art will readily appreciate that changes and/or modifications may be made thereto without departing from the scope of the subject disclosure.

What is claimed is:

1. A deflectable vascular catheter comprising:
   a) a handle assembly;
   b) an elongated sheath extending distally from the handle assembly, the sheath including a deflectable distal end portion;
   c) an actuation mechanism operatively associated with the handle assembly for deflecting the distal end portion of the sheath;
   d) at least one anchor ring located at the deflectable distal end portion of the sheath, wherein the anchor ring has an exterior surface; and
   e) at least one pull wire extending from the actuation mechanism to the at least one anchor ring, wherein the at least one pull wire has a longitudinal axis and a semi-circular cross-sectional shape with a concave inner surface, the concave inner surface contacting the exterior surface of the anchor ring.

2. The deflectable vascular catheter of claim 1, wherein the at least one pull wire is laser welded to the exterior surface of the at least one anchor ring.

3. The deflectable vascular catheter of claim 1, wherein the exterior surface of the at least one anchor ring and the concave inner surface of the at least one pull wire are both cylindrical.

4. The deflectable vascular catheter of claim 1, wherein the at least one pull wire includes a plurality of pull wires.

5. The deflectable vascular catheter of claim 4, wherein one of the plurality of pull wires resides on top of a second one of the plurality of pull wires.

6. The deflectable vascular catheter of claim 5, wherein the first and second ones of the plurality of pull wires are attached at two non-adjacent locations to the exterior surface of the anchor ring.

7. The deflectable vascular catheter of claim 4, wherein each of the plurality of pull wires has a semi-circular cross-sectional shape with a concave inner surface contacting the exterior surface of the anchor ring.

8. The deflectable vascular catheter of claim 4, wherein at least two of the plurality of pull wires have a semi-circular cross-sectional shape with a different concave inner surface contacting the exterior surface of the anchor ring.

9. The deflectable vascular catheter of claim 4, wherein each of the plurality of pull wires has a semi-circular cross-sectional shape with a common concave inner surface contacting the exterior surface of the anchor ring.

10. The deflectable vascular catheter of claim 4, wherein the plurality of pull wires comprises two pull wires that are attached at opposite locations to the exterior surface of the anchor ring.

11. The deflectable vascular catheter of claim 1, wherein the at least one pull wire having the semi-circular cross-sectional shape with the concave inner surface is attached to the exterior surface of the anchor ring at two non-adjacent points.

12. The deflectable vascular catheter of claim 1, wherein the handle assembly has an interior cavity, and wherein the actuation mechanism includes a linear drive screw that is mounted for reciprocal axial movement within the interior cavity of the handle assembly.

13. The deflectable vascular catheter of claim 12, further comprising a rotatable control knob operatively associated with the handle assembly for moving the linear drive screw.

14. A deflectable vascular catheter, comprising:
   a) a handle assembly;
   b) an elongated sheath extending distally from the handle assembly, the sheath including a deflectable distal end portion;
   c) an actuation mechanism operatively associated with the handle assembly for deflecting the distal end portion of the sheath in at least one direction;
   d) an anchor ring located at the deflectable distal end portion of the sheath, wherein the anchor ring has an exterior surface; and
   e) at least one pull wire extending from the actuation mechanism to the exterior surface of the anchor ring, wherein the at least one pull wire has a longitudinal axis and a semi-circular cross-sectional shape with a concave inner surface, the concave inner surface contacting the exterior surface of the anchor ring.

15. The deflectable vascular catheter of claim 14, wherein the at least one pull wire is attached at least two non-adjacent points to the exterior surface of the anchor ring.

16. A deflectable vascular catheter, comprising:
   a) a handle assembly;
   b) an elongated sheath extending distally from the-handle assembly, the sheath including a deflectable distal end portion;
   c) an actuation mechanism operatively associated with the handle assembly for deflecting the distal end portion of the sheath in at least two directions;
   d) an anchor ring located at the deflectable distal end portion of the sheath, wherein the anchor ring has an exterior surface;
   e) a first pull wire extending from the actuation mechanism to a first weld location on the exterior surface of the anchor ring, wherein the first pull wire has a first longitudinal axis and a semi-circular cross-sectional shape with a first concave inner surface, the first concave inner surface contacting the exterior surface of the anchor ring; and
   f) a second pull wire extending from the actuation mechanism to a second weld location on the exterior surface of the anchor ring, wherein the second pull wire has a second longitudinal axis and a semi-circular cross-sectional shape with a second concave inner surface, the second concave inner surface contacting the exterior surface of the anchor ring, and wherein the first and second weld locations are different.

17. The deflectable vascular catheter of claim 16, wherein the exterior surface of the at least one anchor ring and the first and second concave inner surfaces of the first and second pull wires are cylindrical.

* * * * *